United States Patent
Fadell et al.

(10) Patent No.: US 10,970,614 B2
(45) Date of Patent: Apr. 6, 2021

(54) SINGLE-USE PRESSURE TRANSDUCER DISPOSABLE INTERFACE

(71) Applicant: Rosemount Inc., Shakopee, MN (US)

(72) Inventors: Paul R. Fadell, Cypress, TX (US); Nathan Stokes, Chaska, MN (US)

(73) Assignee: Rosemount Inc., Shakopee, MN (US)

( * ) Notice: Subject to any disclaimer, the term of this patent is extended or adjusted under 35 U.S.C. 154(b) by 162 days.

(21) Appl. No.: 16/014,534

(22) Filed: Jun. 21, 2018

(65) Prior Publication Data

US 2019/0392280 A1 Dec. 26, 2019

(51) Int. Cl.

| | |
|---|---|
| *G06K 19/077* | (2006.01) |
| *G01L 9/00* | (2006.01) |
| *C12M 1/00* | (2006.01) |
| *G06K 7/10* | (2006.01) |
| *G01L 19/00* | (2006.01) |
| *C12M 1/34* | (2006.01) |
| *C12M 3/00* | (2006.01) |

(52) U.S. Cl.
CPC ....... *G06K 19/07773* (2013.01); *C12M 23/28* (2013.01); *C12M 41/40* (2013.01); *G01L 9/0041* (2013.01); *G01L 19/003* (2013.01); *G06K 7/10366* (2013.01); *C12M 23/26* (2013.01); *C12M 23/48* (2013.01)

(58) Field of Classification Search
CPC ......... G06K 19/07773; G06K 19/0717; G06K 7/10366; C12M 23/28; C12M 23/26; C12M 23/48; C12M 41/40; C12M 29/00; G01L 9/0041
See application file for complete search history.

(56) References Cited

U.S. PATENT DOCUMENTS

| | | | | |
|---|---|---|---|---|
| 7,151,455 B2* | 12/2006 | Lindsay | ............. | G06K 19/0717 340/572.3 |
| 7,259,675 B2* | 8/2007 | Baker | ................. | G06K 7/0008 340/572.1 |
| 7,784,353 B1* | 8/2010 | Feldmeier | ........... | G01L 19/0023 73/744 |
| 8,138,922 B2* | 3/2012 | Lindsay | ............. | G06K 19/0716 340/539.26 |
| 8,297,128 B2* | 10/2012 | Delbos | ................. | G01J 5/0037 73/756 |
| 8,318,111 B2* | 11/2012 | Mingerink | .......... | B05B 11/0005 206/459.5 |

(Continued)

OTHER PUBLICATIONS

International Search Report and Written Opinion for International Patent Application No. PCT/US2019/037667, dated Oct. 18, 2019, date of filing: Jun. 18, 2019, 11 pages.

(Continued)

*Primary Examiner* — Jonathan M Dunlap
(74) *Attorney, Agent, or Firm* — Christopher R. Christenson; Kelly, Holt & Christenson PLLC

(57) ABSTRACT

A single-use adapter for coupling a single-use container to a reusable sensor transducer includes an attachment region. The single-use adapter includes a deflectable diaphragm sealingly coupling to the attachment region and configured to contact a media sample. The single-use adapter also includes a radio-frequency identification (RFID) tag coupled to the single-use adapter and configured to store and transmit data.

13 Claims, 9 Drawing Sheets

(56) References Cited

U.S. PATENT DOCUMENTS

| | | | | |
|---|---|---|---|---|
| 8,485,044 B2* | 7/2013 | Delbos | ............... | G01J 5/0037 |
| | | | | 73/714 |
| 8,519,846 B2* | 8/2013 | Baker | ............... | G06Q 10/08 |
| | | | | 257/421 |
| 8,640,560 B2 | 2/2014 | Burke | | |
| 8,653,940 B2* | 2/2014 | Nyffeler | ............... | G06K 19/14 |
| | | | | 340/5.8 |
| 8,702,674 B2* | 4/2014 | Bochenko | ............ | A61J 1/2096 |
| | | | | 604/404 |
| 8,963,684 B2* | 2/2015 | Nyffeler | ............ | G06Q 20/3278 |
| | | | | 340/5.8 |
| 9,050,379 B2* | 6/2015 | Selker | ............... | A61L 2/0035 |
| 9,067,014 B2* | 6/2015 | Nelson | ............... | A61M 5/168 |
| 9,746,391 B2* | 8/2017 | Gagne | ............... | G01L 19/14 |
| 9,764,076 B2* | 9/2017 | Gerber | ............... | G06K 19/077 |
| 9,782,506 B2* | 10/2017 | Selker | ............... | A61L 2/0035 |
| 9,996,718 B2* | 6/2018 | Vogel | ............... | G06K 7/10366 |
| 10,089,850 B2* | 10/2018 | Potyrailo | ............... | G08B 21/18 |
| 10,262,170 B2* | 4/2019 | Vogel | ............... | G06K 7/10366 |
| 10,267,701 B2* | 4/2019 | Gagne | ............... | G01L 19/0023 |
| 10,522,025 B2* | 12/2019 | Potyrailo | ............ | G06K 19/0702 |
| 2004/0027912 A1 | 2/2004 | Bibbo et al. | | |
| 2005/0205658 A1* | 9/2005 | Baker | ............... | G06K 7/10079 |
| | | | | 235/375 |
| 2007/0200703 A1* | 8/2007 | Baker | ............... | G06K 7/10079 |
| | | | | 340/572.1 |
| 2008/0024310 A1* | 1/2008 | Baker | ............... | G06K 7/10366 |
| | | | | 340/572.8 |
| 2009/0247989 A1* | 10/2009 | Burke | ............... | C12M 41/00 |
| | | | | 604/533 |
| 2009/0273447 A1* | 11/2009 | Selker | ............... | A61L 2/081 |
| | | | | 340/10.1 |
| 2011/0041619 A1* | 2/2011 | Delbos | ............... | G01J 5/08 |
| | | | | 73/756 |
| 2011/0264069 A1 | 10/2011 | Bochenko | | |
| 2012/0222468 A1 | 9/2012 | Nelson et al. | | |
| 2012/0240686 A1 | 9/2012 | Blomberg et al. | | |
| 2013/0018356 A1* | 1/2013 | Prince | ............... | G06Q 10/0833 |
| | | | | 604/506 |
| 2015/0061282 A1* | 3/2015 | Faldt | ............... | A61M 39/105 |
| | | | | 285/124.5 |
| 2015/0137992 A1* | 5/2015 | Potyrailo | ............... | G08B 21/18 |
| | | | | 340/870.07 |
| 2015/0306267 A1* | 10/2015 | Selker | ............... | A61L 2/24 |
| | | | | 340/10.42 |
| 2015/0323486 A1* | 11/2015 | Schick | ............... | G01N 27/4167 |
| | | | | 204/403.02 |
| 2015/0359954 A1* | 12/2015 | Gerber | ............... | A61M 1/36 |
| | | | | 210/647 |
| 2016/0017269 A1* | 1/2016 | Ferguson | ............... | C12M 41/00 |
| | | | | 435/287.1 |
| 2016/0148027 A1* | 5/2016 | Schoutens | ........ | G06K 19/07749 |
| | | | | 340/10.1 |
| 2016/0245714 A1* | 8/2016 | Gagne | ............... | G01L 19/0038 |
| 2017/0068832 A1* | 3/2017 | Vogel | ............... | G06K 7/10366 |
| 2017/0124845 A1* | 5/2017 | Potyrailo | ............... | A61L 2/24 |
| 2017/0281921 A1* | 10/2017 | Faldt | ............... | A61M 39/18 |
| 2017/0322100 A1* | 11/2017 | Gagne | ............... | G01L 19/14 |
| 2018/0049947 A1* | 2/2018 | Brandenburger | ..... | A61J 1/1412 |
| 2018/0253575 A1* | 9/2018 | Vogel | ............... | G06K 19/07745 |
| 2019/0043333 A1* | 2/2019 | Potyrailo | ............... | G08B 21/18 |

OTHER PUBLICATIONS

First Chinese Office Action dated Oct. 12, 2020 for Chinese patent appticafion No. 201811206669.0, 21 pages including English translation.

* cited by examiner

SINGLE-USE PRESSURE TRANSDUCER DISPOSABLE INTERFACE

BACKGROUND

Single-use containers, such as bioreactors, are useful for generating and supporting biological reactions for any number of purposes. Biological reactions can be susceptible to changes in temperature and/or pressure. Moreover, as the biological reaction progresses, the reaction itself may change various parameters within the bioreactor, such as the pressure. Accordingly, it may be important to monitor pressure or other variables of the biological reaction.

The life sciences industry is moving from large, capital-intensive facilities made of stainless steel with large clean-in-place (CIP) infrastructure to smaller facilities that use polymeric bags or containers functioning as bioreactors. The bioreactor bag is used once and then discarded. This single-use bioreactor technique significantly reduces the capital cost of the plant. For example, in existing facilities that use stainless steel CIP infrastructure, up to 90% of the cost of operating the facility may be due to the clean-in-place infrastructure, including very high end instrumentation designed to withstand a steam cleaning cycle. By moving to disposable, single-use bioreactor bags, the CIP portion of the capital can be eliminated and the facility can be more flexible and much smaller, which, in turn, allows the production of the smaller batches that are needed for more targeted drug therapies and other smaller-scale applications.

As pharmaceutical manufacturers change over from large stainless-steel process vessels to smaller-volume, pre-sterilized, disposable plastic bag systems, there is a need to measure pressure and/or other variables in these systems to control the growth environment and subsequent processes. Typically, pharmaceutical manufacturers and the life science industry, in general, have used pressure sensors that are pre-sterilized and are disposed of after a single-use, which, in turn, has driven the life sciences industry to use inexpensive sensors. Such inexpensive sensors use relatively crude methods for fluid isolation, such as silicone gel. These methods can lead to inaccurate measurements, which are generally unacceptable to the life sciences industry for supporting the various biological reactions.

SUMMARY

A single-use adapter for coupling a single-use container to a reusable sensor transducer includes an attachment region. The single-use adapter includes a deflectable diaphragm sealingly coupling to the attachment region and configured to contact a media sample. The single-use adapter also includes a radio-frequency identification (RFID) tag coupled to the single-use adapter and configured to store and transmit data.

DETAILED DESCRIPTION OF ILLUSTRATIVE EMBODIMENTS

In accordance with an embodiment of the present invention, an adapter is provided that provides an interface between a sensor transducer and a media sample from a single-use container. In one example, the adapter allows the sensor transducer to monitor a parameter of the media sample, via a diaphragm of the adapter, while maintaining the media integrity within the single-use container. However, it is contemplated that the adapter maintains the media integrity with or without the sensor transducer connected to the adapter. Additionally, the adapter also protects the sensor transducer from adverse effects stemming from direct contact with the media (such as corrosion), while also protecting the single use container from any external contamination.

Furthermore, embodiments of the present invention include a single-use adapter with a simplified and improved mechanical interface that allows for a confirmation of sensor installation and material traceability. In one example, this includes a single-use adapter with an RFID tag storing material traceability information, lot information, or any suitable configuration information. In operation, the RFID tag within the adapter may be a passive tag with an open antenna circuit, with an antenna coil and a switch, that is configured to be closed upon physically coupling a sensor transducer to the adapter. In this example, upon physically coupling a sensor transducer to the adapter, the antenna circuit is closed, via conductive contacts on the adapter, and can receive radio frequency (RF) energy from an RF reader. Upon receiving the RF energy, the RF tag can subsequently supply the information within the RFID tag to the RF reader. Based on the received information resulting from the closed antenna circuit, the sensor transducer can generate an indication of a successful coupling between the single-use adapter and the sensor transducer. While a RFID tag is mentioned, it is expressly contemplated that the RFID tag may be active or passive, and, in certain embodiments, may be an NFC tag as well.

In one example, an improved mechanical interface includes at least one coupling, or snap-in, mechanism that allows either the adapter or the sensor transducer to click-lock into place and be subsequently removed via a tear-away feature or finger squeeze lever. Additionally, the adapter may include a retention feature configured to enable the adapter to withstand a greater internal pressure prior to being coupled to a sensor transducer. This may allow the diameter and, thus, cost of the adapter to be reduced while still meeting pressure handling requirements. This may include manufacturing the adapter using various polymers or plastics that can be sterilized as a single piece. However, these are simply examples of a number of improved mechanical features within the context of the present invention.

Figure 1:
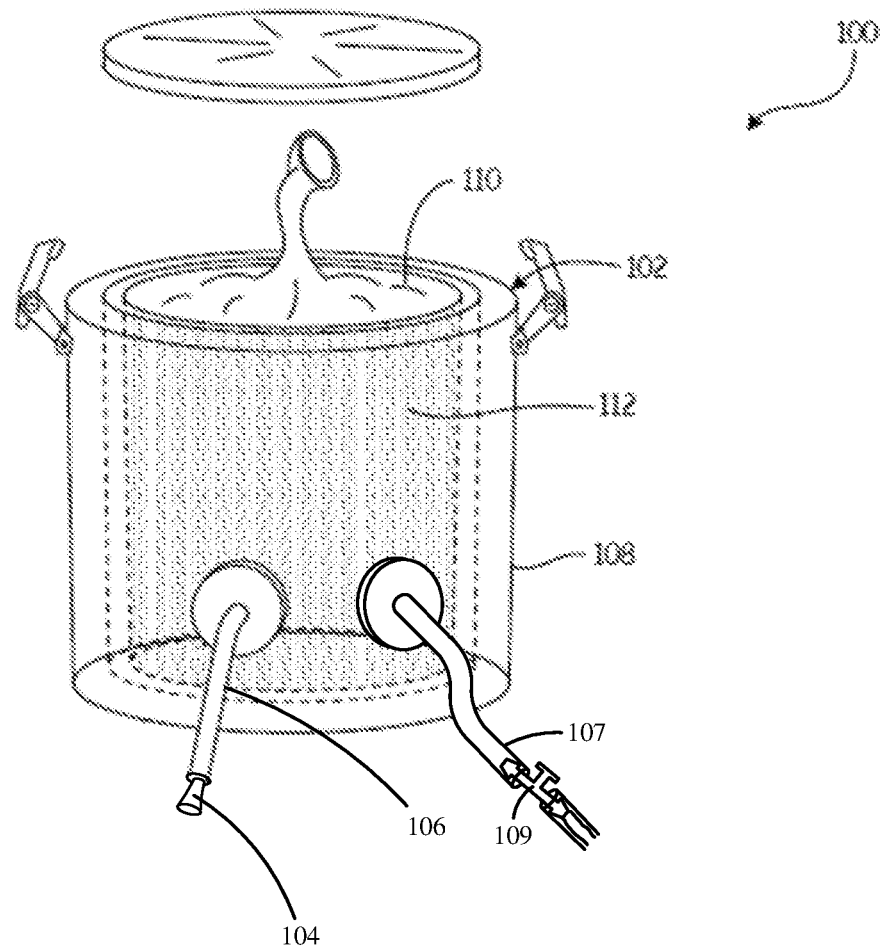
FIG. 1 is a diagrammatic view of a single-use container, such as a bioreactor, and an adapter in accordance with an embodiment of the present invention.

FIG. 1 is a diagrammatic view of a single-use container, such as a bioreactor, and an adapter in accordance with an embodiment of the present invention. Bioreaction system 100 includes a bioreactor 102, configured to carry out a biological reaction, coupled to adapters 104, 109 via fluidic coupling mechanisms 106, 107 respectively. However, in other examples, it is contemplated that bioreaction system 100 may only be coupled to adapter 104 or 109. While fluidic coupling mechanisms 106, 107 illustratively includes a tube, a variety of other mechanisms may be used as well, such as a connection port.

Bioreactor 102 illustratively includes an outer support container 108 with a wall that is relatively solid such that it forms a shell for a single-use bioreaction bag 110 disposed therein. Support container 108 is generally matched to the dimensions and functionality of single-use bioreaction bag 110 to support a biological sample 112 configured to undergo a reaction within bioreaction bag 110. In operation, support container 108 is typically a reusable item, while single-use bioreaction bag 110 is generally a polymeric bag that is disposed of after a biological reaction occurs within sample 112.

In operation, adapters 104, 109 are configured to serve as an interface between biological sample 112, within bioreactor 102, and measurement instruments, such as sensor transducers, configured to measure a parameter of the media sample. This involves simultaneously coupling adapters 104, 109 to fluidic coupling mechanisms 106, 107, illustratively shown as tubes, and the measurement instruments such that the measurement instruments can monitor a parameter of biological sample 112 without directly contacting biological sample 112 and/or fluidic coupling mechanisms 106, 107. This will be discussed further in the context of FIGS. 3-9. Additionally, fluidic coupling mechanisms 106, 107 can include a hose, tube or any other mechanism that allows the measurement instruments to monitor a parameter, such as pressure, of biological sample 112 upon being coupled to adapters 104, 109. Additionally, in this example, adapter 109 can be a downstream connector that allows a measurement instrument to measure a parameter of the media sample as the media sample moves downstream for further processing. This may include harvesting, filtration, etc.

Figure 2:
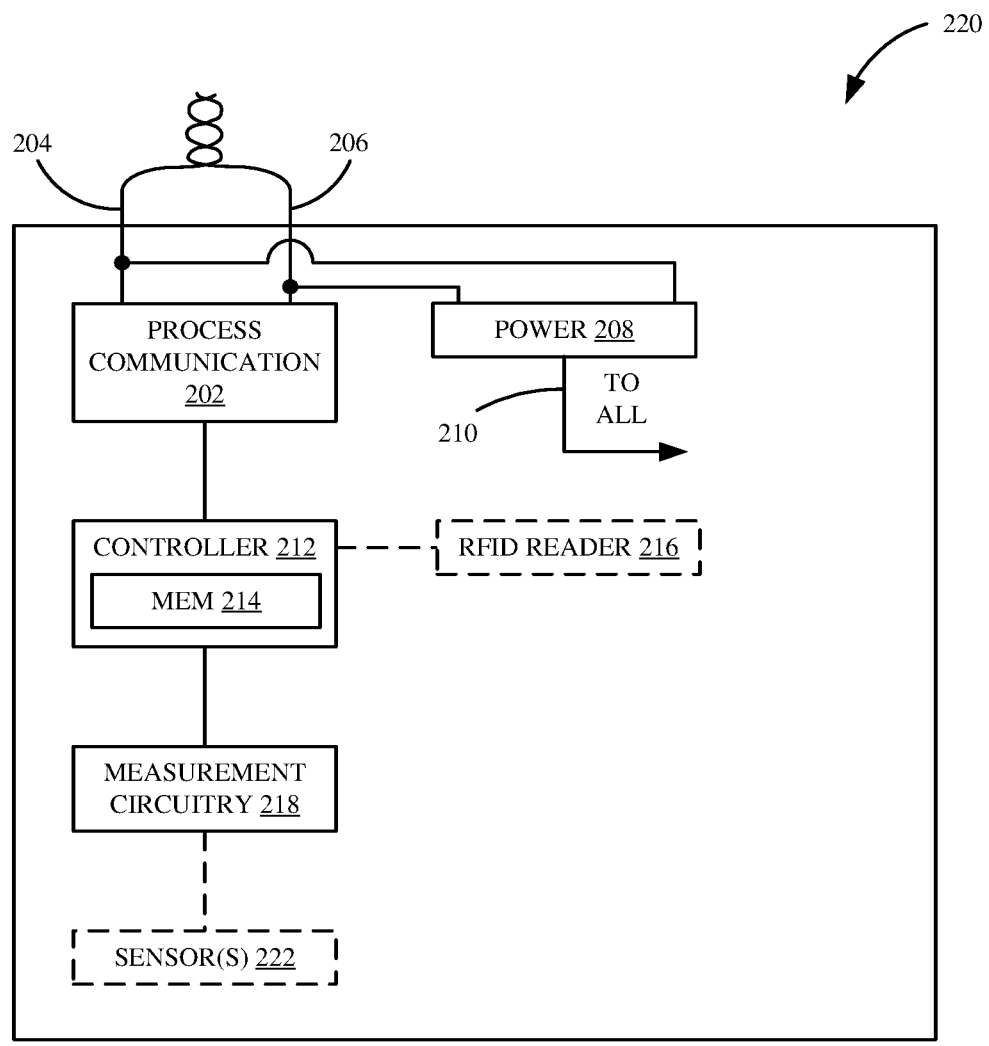
FIG. 2 is a block diagram of a measuring instrument, such as a sensor transducer, in more detail.

FIG. 2 is a block diagram of a measurement instrument, such as a sensor transducer, in more detail. Measurement instrument 220 can measure a wide variety of different parameters of a biological sample which can include temperature, pressure, dissolved oxygen, pH, etc. Additionally, measurement instrument 220 can include characterization and/or calibration information to compensate for variations in temperature and/or other environmental variables. Measurement instrument 220 can also perform diagnostics relative to itself and/or a biological sample to provide additional information outside of simply the measured parameter.

Measurement instrument 220 includes process communication circuitry 202, a power module 208, a controller 212 with memory 214, an optional radio-frequency identification (RFID) reader 216, measurement circuitry 218 and sensor(s) 222. In one embodiment, process communication circuitry 202 is configured to be coupled to a process communication loop or segment via a plurality of conductors 204, 206. Upon being coupled to the process communication loop or segment, measurement instrument 220 can convey information to one or more additional devices via the process communication loop or segment in accordance with the Highway Addressable Remote Transducer (HART®) protocol or the FOUNDATION™ Fieldbus protocol. In other embodiments, process communication circuitry can communicate wirelessly using any suitable wireless communication protocols, such as IEC 62591.

Power module 208 is coupled to conductors 204, 206 and, in some embodiments, is configured to receive energization power from conductors 204, 206 such that suitable power can be provided to various components within measurement instrument 220. This is generally indicated by arrow 210 labeled "To All."

As illustratively shown, controller 212 is coupled to process communication circuitry 202, measurement circuitry 218 and optional RFID reader 216 such that information received from measurement circuitry 218 and/or RFID reader 216 can be communicated over a process communication loop or in accordance with a wireless communication protocol. Additionally, controller 212 may include, or be coupled to, suitable memory 214 which can store program data as well as process data. Memory 214 may include volatile and/or non-volatile memory. In one embodiment, controller 212 is a microprocessor with suitable memory 214 such that controller 212 is able to programmatically execute a series of program steps in order to serve its function as a measurement instrument 220.

Measurement circuitry 218 is coupled to one or more sensors 222, such as a pressure sensor, to sense a sample parameter within the bioreactor. Measurement circuitry 218 includes, in some embodiments, one or more analog-to-digital converters, linearization and/or amplification circuitry, and provides an indication of one or more sensed analog values to controller 212 in the form of a digital signal. Controller 212 receives the digital signal from measurement circuitry 218 and programmatically calculates one or more process variables that may be made available over a process communication loop or segment.

Sensor(s) 222 may be disposed within measurement instrument 220, such as a pressure sensor disposed within a sensor transducer, or may be disposed external to measurement instrument 220 and coupled thereto via suitable wiring. Sensor(s) 222 are configured to generate an analog signal, indicative of a media parameter, and provide the signal to measurement circuitry 218.

RFID reader 216 may be coupled to controller 212 and enables controller 212 to communicate in accordance with known RFID techniques. RFID reader 216 is, in some embodiments, configured to power a passive RFID tag or device that is disposed within an adapter as will be discussed in FIGS. 3-6. Briefly, however, upon powering an RFID tag within an adapter, controller 212 can receive traceability and lot information, or any other configuration information stored within the RFID tag regarding a media sample within a single-use container. Additionally, in embodiments where the RFID antenna circuit is closed upon physically coupling the adapter to the sensor transducer, RFID communication will provide confirmation of such successful coupling.

While embodiments of the present invention will generally be described with respect to an active RFID reader powering a passive RFID tag within an adapter, it is expressly contemplated that embodiments can be practiced using two "active" RFID devices communicating with one another. Further, while RFID reader 216 is illustratively shown within measurement instrument 220, it is also contemplated that RFID reader 216 may be external to measurement instrument 220 and used to power the RFID tag within the adapter.

Figure 3:
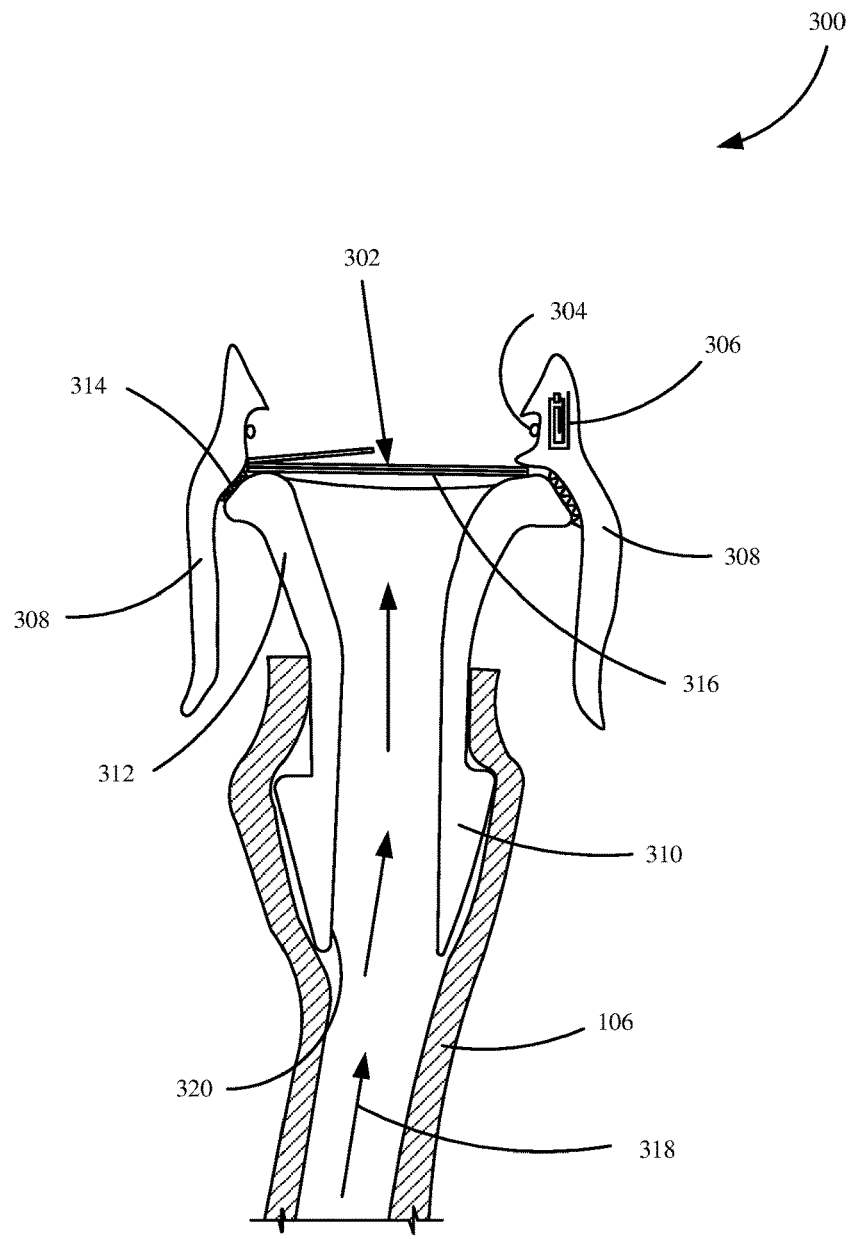
FIG. 3 is a diagrammatic view of an adapter with an attachment region and a diaphragm coupled to a fluidic coupling mechanism in accordance with an embodiment of the present invention.

FIG. 3 is a diagrammatic view of adapter 300 with an attachment region 312 and a diaphragm 316 coupled to a fluidic coupling mechanism 106 in accordance with an embodiment of the present invention. In one example, adapter 300 is configured to serve as an interface between a received media sample from a single-use container and a measurement instrument configured to measure a parameter of the received media sample. In operation, this involves simultaneously coupling adapter 300 to both fluidic coupling mechanism 106, illustratively shown as a tube, and a measurement instrument, such as measurement instrument 220.

Adapter 300 illustratively includes an attachment region 312 with passageway 320, barbs 310, deflectable diaphragm 316, RFID tag 306 with contacts 304, pressure retention feature 302 (shown in greater detail in FIG. 7), and coupling mechanisms 308 coupled to attachment region 312 via an ultrasonic or thermal weld 314.

In operation, attachment region 312 of adapter 300 couples to fluidic coupling mechanism 106, via barbs 310, and receives a media sample from a single-use container generally in the direction of arrows 318. A received media sample then travels through passageway 320 of attachment region 312 and comes into contact with an interior of deflectable diaphragm 316. In turn, a measurement instrument, e.g. measurement instrument 220 shown in FIG. 2, coupled to an exterior of diaphragm 316 can measure a parameter, such as pressure, of the sample based on a characteristic change in diaphragm 316.

In this configuration, a measurement instrument, such as a sensor transducer, is able to measure a parameter of the media sample, such as pressure, without directly contacting the media itself. As a result, a relatively high precision measurement instrument can obtain a high-quality process fluid measurement and provide an indication thereof to monitoring and/or control equipment without contacting the media directly. In this fashion, a process sensor and transmitter can be reused after being coupled to adapter 300, enabling the measuring instrument to be a relatively complex and feature-rich device that is able to carry out a number of functions such as linearization, digital communication, alarm detection and annunciation, etc.

Deflectable diaphragm 316 can be formed of any suitable material that is suited for exposure to the media and is able to allow a measurement instrument coupled on an opposite side thereof to transduce meaningful information relative to the media. This may include one uniform material or a plurality of different materials. For example, an interior of diaphragm 316 may be formed of a different material compared to an exterior of diaphragm 316. Example materials can include silicone rubber, polytetrafluoroethylene (PTFE), Ultra-Low, Very-Low, Low, Medium, High, and Very-High Durometer Urethane, Nylon, Polyethylene Terephthalate (PET), and Pebax®.

However, prior to physically coupling diaphragm 316 to a measurement instrument, adapter 300 may include pressure retention feature 302 that allows for an increased pressure retention capability compared to what diaphragm 316 can withstand alone. For example, retention feature 302 can be a "tear-away" support cap that is manufactured proximate diaphragm 316 and allows for an increased pressure retention capability, up to 5 pounds per square inch (psi) in one example, prior to coupling diaphragm 316 to the measurement instrument. In this example, pressure retention feature 302 can be removed (i.e. torn away) just prior to coupling diaphragm 316 to the measurement instrument. This will be discussed further in FIG. 7.

Adapter 300 couples to a measurement instrument using coupling features 308. Coupling features 308 are snap-in features that allow the measurement instrument to click-lock into place on adapter 300, and, subsequently, allow the measurement instrument to be released from adapter 300 by a finger squeeze lever.

In operation, upon aligning the measurement instrument to adapter 300, an insertion force may be applied to the measurement instrument until a flange of the measurement instrument is received by coupling features 308. Once received, the measurement instrument is securely fastened proximate diaphragm 316. To release the measurement instrument, a pressure may be applied to coupling features 308 allowing the measurement instrument to be removed from adapter 300. This is but one example and is illustratively shown in FIG. 5. Additionally, while it is shown in FIGS. 3 and 5 that coupling features 308 are coupled to adapter 300, it is also contemplated that coupling features 308 may be coupled to measurement instrument as illustratively shown in FIG. 4.

During manufacture, coupling features 308 can be coupled to attachment region 312 via ultrasonic welds 314 or any other suitable manufacturing techniques. In the circumstance both attachment region 312 and coupling features 308 are made of plastic, ultrasonic weld 314 allows for a secure attachment between the pieces through an application of high-frequency ultrasonic acoustic vibrations while the collective pieces are under pressure. This allows for a relatively less expensive design and manufacture for adapter 300.

Adapter 300 also includes RFID tag 306 with contacts 304. In one embodiment, RFID tag 306 is a passive RFID tag that includes an RFID chip with any or all information pertaining to material traceability and/or lot information, and an antenna circuit with an antenna coil and switch configured to supply power received from a RFID reader, e.g. RFID reader 216 within measurement instrument 220, to the RFID chip. Upon receiving power from the antenna circuit, the RFID chip within tag 306 is able to provide the information to the RFID reader, such as reader 216 (shown in FIG. 2). The information may then be transmitted over a process communication loop and/or stored by the measurement instrument.

Once the information is received from RFID tag 306, a controller of the measurement instrument can generate and provide an indication of a correct coupling between adapter 300 and the measurement instrument. For example, the antenna circuit of RFID tag 306 may be an open circuit, with exposed contacts 304, that is configured to be closed upon physically coupling the measurement instrument to adapter 300. In this embodiment, if no measurement instrument is coupled to adapter 300, the antenna circuit remains open and cannot supply power to the RFID chip. As a result, no information can be received from RFID tag 306.

However, upon physically coupling a measurement instrument to adapter 300, the antenna circuit is closed and can receive power from a RFID reader. Power can then be supplied from the antenna circuit to the RFID chip such that information can be provided to the RFID reader. Once received, the controller of measurement instrument can generate an indication of a successful coupling between adapter 300 and the measurement instrument based on the successfully received information from the RFID chip.

Additionally, while RFID tag 306 is illustratively shown coupled to coupling features 308, it is contemplated that RFID tag 306 may be coupled to other features of adapter 300. Furthermore, it is contemplated that RFID tag 306 can be sterilized along with adapter 300, or alternatively, as part of an assembly with adapter 300 coupled to fluidic coupling mechanism 106. This can include exposure to gamma radiation in one example. In one embodiment, tag 306 is a commercially available RFID tag sold under the trade designation GammaTag® available from Verigenics, of Southampton, Pa.

Figure 4:
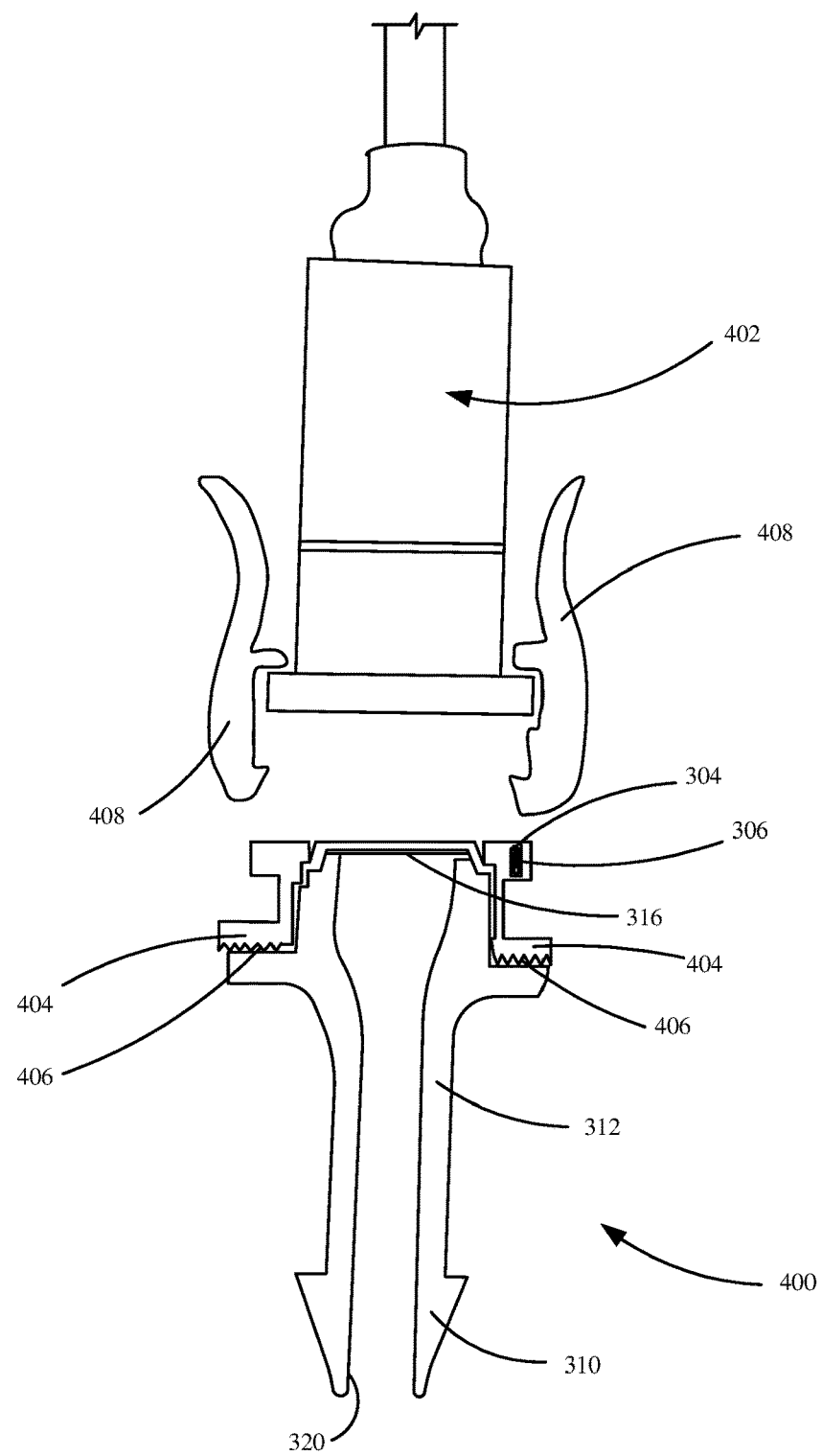
FIG. 4 is a diagrammatic view of an adapter and a sensor transducer in accordance with an embodiment of the present invention.
Figure 5:
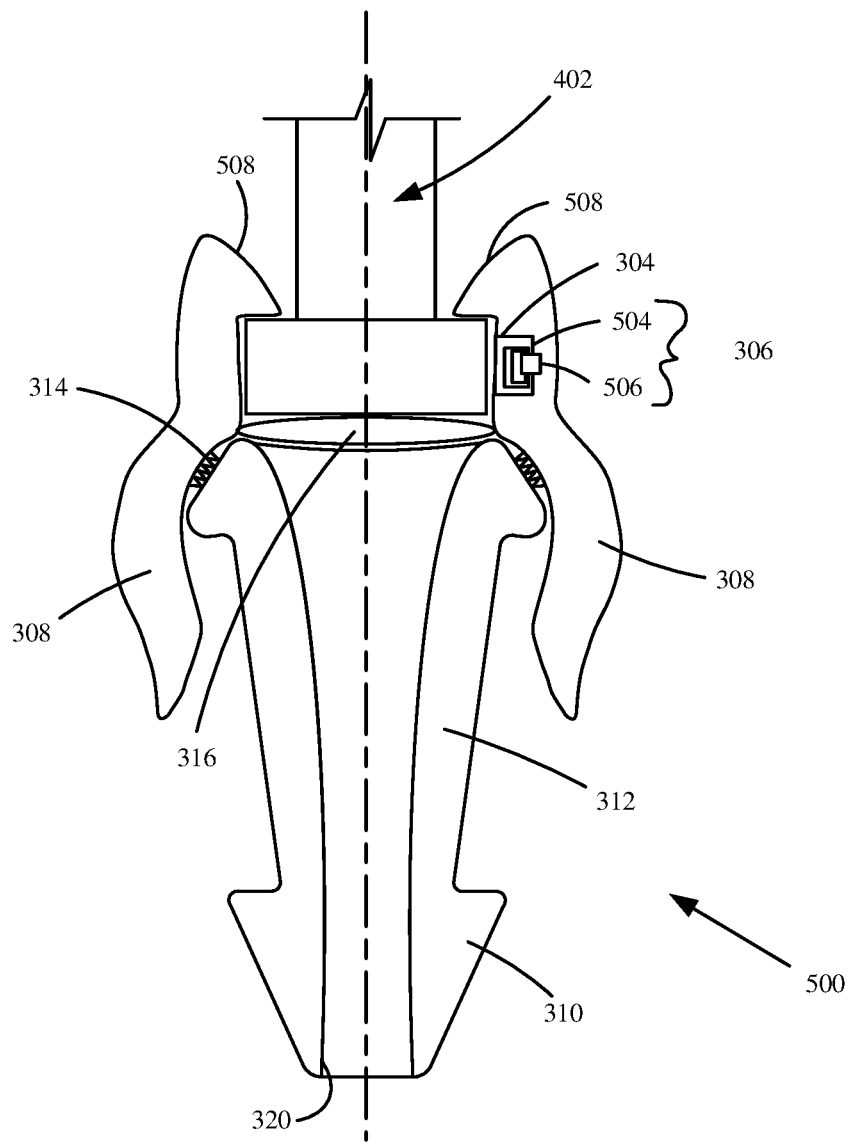
FIG. 5 is a diagrammatic view of an adapter assembly in accordance with an embodiment of the present invention.

FIG. 4 is a diagrammatic view of an adapter and a sensor transducer in accordance with an embodiment of the present invention. As illustratively shown, adapter 400 includes many of the same features as shown in FIG. 3. However, as illustratively shown in this embodiment, coupling features 408 are coupled to measurement instrument 402 rather than adapter 400. Coupling features 408 may be the same or different than coupling features 308 shown in FIG. 3. In this embodiment, adapter 400 includes a receiving portion 404 that is configured to couple to coupling features 408 on measurement instrument 402. Once coupling features 408 are coupled to receiving portion 404, measurement instrument 402 is securely fastened to adapter 400 and can measure a parameter of a media sample via a characteristic change in diaphragm 316. Additionally, receiving portion 404 may be fixed to attachment region 312 via ultrasonic or thermal welds 406.

FIG. 5 is a diagrammatic view of an adapter assembly in accordance with an embodiment of the present invention. Adapter assembly includes adapter 500 securely coupled to measurement instrument 402. As illustratively shown, adapter 500 is securely fastened to measurement instrument 402 via a coupling between coupling features 308 and a flange of measurement instrument 402. In this embodiment, tapered portions 508 of coupling features 308 can physically couple to the flange thereby securing measurement instrument 402 to adapter 500.

As illustratively shown, adapter 500 includes RFID tag 306 with a RFID chip 506 and an open antenna circuit 504 with exposed contacts 304. Exposed contacts 304, in one embodiment, may be made of a conductive plastic. While exposed contacts 304 are illustratively exposed on a single coupling feature, in other embodiments, exposed contacts 304 may be located at various locations within adapter 500. Upon physically coupling measurement instrument 402 to adapter 500, antenna circuit 504 is configured to be closed and can direct power received from an RFID reader, within measurement instrument 402, to RFID chip 506. RFID chip 506 may then supply any information within RFID chip 506 to measurement instrument 402. Additionally, a confirmation signal may be generated by measurement instrument 402 indicative of a successful coupling between adapter 500 and measurement instrument 402 based on closed antenna circuit 504.

Figure 6:
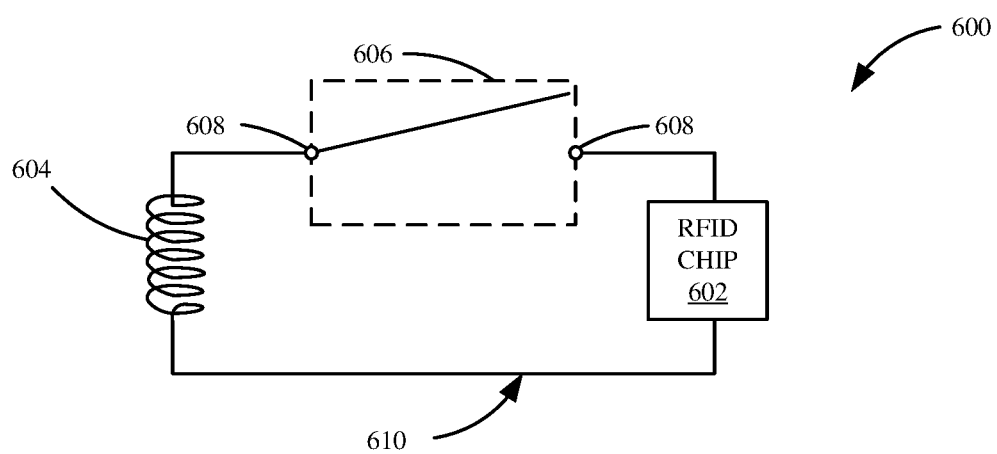
FIG. 6 is a diagrammatic view of a radio frequency identification (RFID) tag within an adapter in accordance with an embodiment of the present invention.

FIG. 6 is a diagrammatic view of a radio frequency identification (RFID) tag within an adapter in accordance with an embodiment of the present invention. RFID tag 600 includes RFID chip 602 and an open antenna circuit 610. Antenna circuit 610 includes an antenna coil 604 connected to a switch 606 with contacts 608. In operation, RFID chip 602 includes any or all traceability data, lot information and/or configuration information, and, upon receiving energy from antenna coil 604, supplied from a RFID reader, communicates the information to the RFID reader. However, in this embodiment, switch 606 is connected to antenna coil 604 and is configured to remain open until the adapter is physically coupled to a sensor transducer. Upon physically coupling the sensor transducer to the adapter, switch 606 is closed enabling antenna coil 604 to provide energy to RFID chip 602. In turn, RFID chip 602 can supply the information to the RFID reader while indicating a successful physical coupling between the adapter and the sensor transducer. In one example, a confirmation signal is generated and provided over a process communication loop indicative of the physical coupling.

Figure 7:
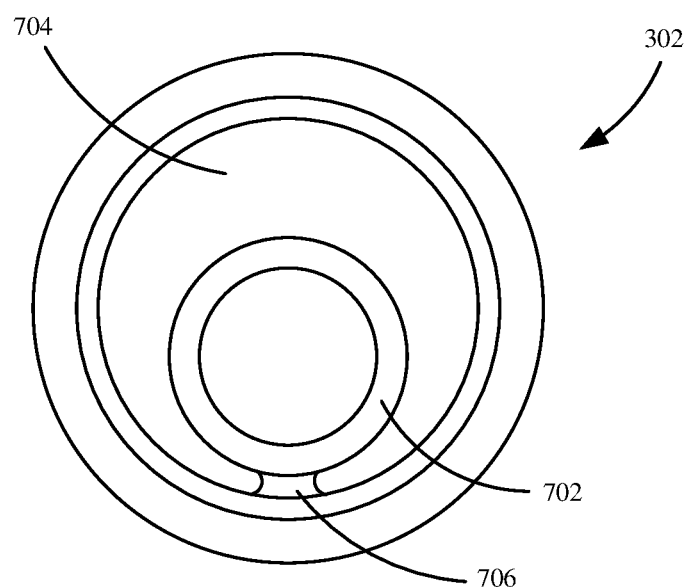
FIG. 7 is a diagrammatic view of a pressure retention feature of a single-use adapter in accordance with an embodiment of the present invention.

FIG. 7 is a diagrammatic view of a pressure retention feature of a single-use adapter in accordance with an embodiment of the present invention. Pressure retention feature 302 is configured to securely couple to adapter 300, proximate diaphragm 316, during manufacture to allow the adapter to withstand a greater internal pressure than could be borne by diaphragm 316 alone. In operation, prior to coupling the adapter to a measurement instrument, retention feature 302 can be removed such that a diaphragm of the adapter is exposed for contact with the measurement instrument.

Pressure retention feature 302 includes a cap 704, a connecting member 706 and a circular member 706. During operation, cap 704 can rest on a diaphragm and allow adapter to have a greater internal pressure retaining capability. To remove retention feature 302, a pulling force may be applied to circular member 706 which, in turn, decouples cap 704 from the diaphragm. Once removed, retention feature 302 may be discarded and the adapter coupled to a measurement instrument.

Figure 8:
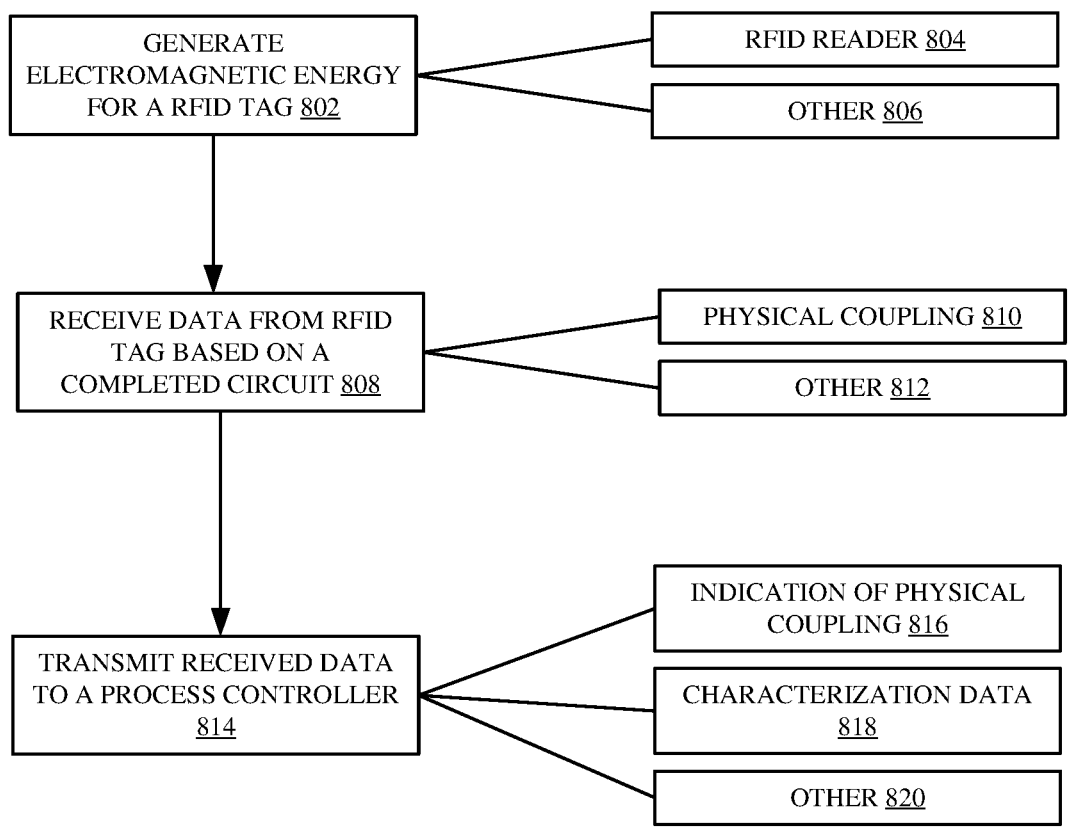
FIG. 8 is a flow diagram showing one example of receiving information from a RFID tag in accordance with an embodiment of the present invention.

FIG. 8 is a flow diagram showing one example of receiving information from an RFID tag in accordance with an embodiment of the present invention. Method 800 may be useful for obtaining information regarding material traceability and lot information, among a variety of other configuration information for single-use applications. Method 800 begins at block 802 where electromagnetic energy is generated for a RFID tag within an adapter. In one embodiment, electromagnetic energy is generated by an RFID reader within a measurement instrument, such as a sensor transducer, configured to couple to the adapter as indicated by block 804. However, a RFID reader may be placed in a variety of other devices as well as indicated by block 806.

At block 808, data pertaining to material traceability and lot information is received from a RFID tag within an adapter. In one example, data may be received based on a physical coupling between the adapter and a measurement instrument such that an antenna circuit within the RFID tag is closed, allowing the RFID tag to receive the generated electromagnetic energy from the RFID reader. However, other ways of closing an antenna circuit within a RFID tag are contemplated as well as indicated by block 812.

At block 814, information received from an RFID tag are provided to a process controller. This can include lot information, material traceability information and a wide variety of other configuration information as well. Additionally, an indication of a secure coupling between an adapter and measurement instrument can be generated and provided to a process controller based on the closed antenna circuit. This is indicated by block 816. However, a variety of other data can be provided as well, as indicated by block 820.

As such, a single-use adapter is provided with a simplified and improved mechanical interface that allows for confirmation of sensor installation and material traceability. Additionally, the single-use adapter maintains a media integrity while allowing a sensor transducer to monitor a parameter of a media sample within a single-use container.

Figure 9:
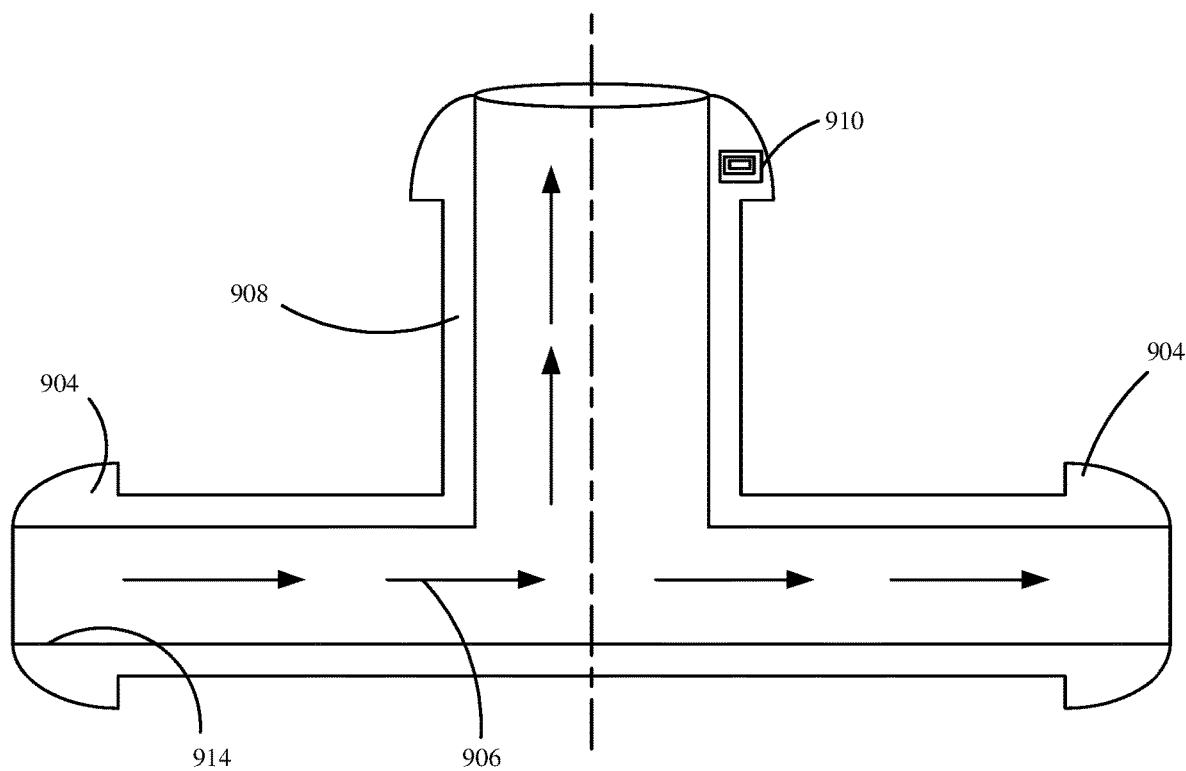
FIG. 9 is a diagrammatic view of an adapter with an attachment region and a diaphragm in accordance with an embodiment of the present invention.

FIG. 9 is a diagrammatic view of an adapter with an attachment region and a diaphragm in accordance with an embodiment of the present invention. Adapter 900 illustratively includes an attachment region 908, with barbs 904 and an RFID tag 910, coupled to a diaphragm 902. In operation, upon coupling barbs 904 to fluidic coupling mechanisms, e.g. tubes, hoses, etc., adapter 900 can receive a flow of media, generally in the direction 906, through passageway 914. In one example, the flow of media is configured to move from a bioreactor to another system for downstream processing, that, in one example, can include filtration, harvesting, etc. While the flow of media travels through passageway 914, a measurement instrument coupled to diaphragm 902 can measure a parameter of the flow of media. This can include temperature, pressure, pH, etc. Additionally, by physically coupling the measurement instrument to diaphragm 902, the measurement instrument can close an open antenna circuit of RFID tag 910 via exposed contacts 912. In one example, this can indicate a successful coupling between adapter 900 and the measurement instrument.

Although the present invention has been described with reference to preferred embodiments, workers skilled in the art will recognize that changes may be made in form and detail without departing from the spirit and scope of the invention.

What is claimed is:

1. A single-use adapter for coupling a single-use container to a reusable sensor transducer, the single-use adapter comprising:
   an attachment region;
   a deflectable diaphragm sealingly coupled to the attachment region and configured to contact a media sample;
   a radio-frequency identification (RFID) tag within the single-use adapter and configured to store and transmit data; and
   wherein the RFID tag comprises an open antenna circuit, with exposed contacts, configured to be closed upon physically coupling the adapter to the sensor transducer, wherein, upon closing, the antenna circuit is configured to receive radio frequency energy from an RFID reader.

2. The single-use adapter of claim 1, wherein the data comprises traceability data.

3. The single-use adapter of claim 1, wherein the data comprises lot information.

4. The single-use adapter of claim 1, wherein the data comprises configuration information.

5. The single-use adapter of claim 1, wherein the contacts comprise a conductive plastic material exposed on the adapter surface.

6. The single-use adapter of claim 1, wherein, upon closing the open antenna circuit through the physical coupling between the adapter to the sensor transducer, a confirmation signal is generated indicative of the physical coupling between the adapter and the sensor transducer.

7. The single-use adapter of claim 1, wherein the RFID tag is configured to be sterilized along with the adapter prior to coupling the adapter to the sensor transducer.

8. The single-use adapter of claim 1, further comprising:
   a retention feature, disposed proximate the diaphragm, the retention feature configured to be decoupled from the adapter to expose the diaphragm prior to coupling the diaphragm to the sensor transducer.

9. The single-use adapter of claim 8, wherein the diaphragm is configured to withstand 5 psi of internal pressure prior to being coupled to the sensor transducer.

10. The single-use adapter of claim 1, further comprising:
    a coupling mechanism, coupled to a connector region, configured to physically couple the adapter to the sensor transducer.

11. The single-use adapter of claim 10, wherein the coupling mechanism is coupled to the connector region via an ultrasonic or thermal weld.

12. A single-use adapter for coupling a single-use container to a reusable sensor transducer, the single-use adapter comprising:
    an attachment region;
    a deflectable diaphragm sealing coupled to the attachment region and configured to contact a media sample;
    a radio-frequency identification (RFID) tag within the single-use adapter and configured to store and transmit data; and
    a retention feature, disposed proximate the diaphragm, the retention feature configured to be decoupled from the adapter to expose the diaphragm prior to coupling the diaphragm to the sensor transducer.

13. The single-use adapter of claim 12, wherein the diaphragm is configured to withstand 5 psi of internal pressure prior to being coupled to the sensor transducer.

* * * * *

UNITED STATES PATENT AND TRADEMARK OFFICE
CERTIFICATE OF CORRECTION

| | |
|---|---|
| PATENT NO. | : 10,970,614 B2 |
| APPLICATION NO. | : 16/014534 |
| DATED | : April 6, 2021 |
| INVENTOR(S) | : Paul R. Fadell and Nathan Stokes |

It is certified that error appears in the above-identified patent and that said Letters Patent is hereby corrected as shown below:

In the Claims

Column 9, Line 40, Claim 1, delete "the antenna circuit,"

Column 10, Line 33, Claim 12, delete "sealing" and insert --sealingly--

Signed and Sealed this
Fifteenth Day of November, 2022

*Katherine Kelly Vidal*

Katherine Kelly Vidal
*Director of the United States Patent and Trademark Office*